United States Patent [19]

Duemmen

[11] Patent Number: Plant 6,716

[45] Date of Patent: Apr. 4, 1989

[54] GERANIUM PLANT NAMED PRAELUDIUM

[76] Inventor: Guenter Duemmen, 4134 Rheinberg 4, Dammweg 18-20, Fed. Rep. of Germany

[21] Appl. No.: 110,771

[22] Filed: Oct. 21, 1987

[30] Foreign Application Priority Data

Apr. 24, 1987 [IT] Italy ..... 099 NV/87

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Marks Murase & White

[57] ABSTRACT

A new and distinct geranium plant known by the cultivar name Praeludium is characterized by an intensive-red colored flower, a semi-double flower form, a dark green foliage with a slight zonation, a robust foliage, a large umbel, and a good rooting pattern.

1 Drawing Sheet

BACKGROUND OF THE NEW PLANT

The present invention comprises a new and distinct cultivar of geranium, botanically known as *Pelargonium zonale,* hereinafter referred to by the cultivar name Praeludium.

Praeludium is a product of a planned breeding program which had the objective of creating new geranium cultivars with an intensive-red colored flower, large umbel, and robust and dark green foliage with a slight zonation.

Praeludium was originated from a hybridization made in a controlled breeding program in Rheinberg, FRG, in 1982–83. The female parent was an unnamed seedling. The male parent of Praeludium was also an unnamed seedling.

Praeludium was discovered and selected as one flowering plant within the progeny of the stated cross by Guenter Duemmen in 1984 in a controlled environment in Rheinberg.

The first act of asexual reproduction of Praeludium was accomplished when vegetative cuttings were taken from the initial selection in July 1984 in a controlled environment in Rheinberg by a technician working under formulations established and supervised by Guenter Deummen. Horticultural examination of selected units initiated in July 1984 has demonstrated that the combination of characteristics as herein disclosed for Praeludium are firmly fixed and are retained through successive generations of asexual reproduction.

Praeludium has not been observed under all possible environmental conditions. The phenotype may vary significantly with variations in environment such as temperature, light intensity, and day length. The following observations, measurements, and comparisons describe plants grown in Rheinberg under greenhouse conditions which approximate those generally used in commercial practice.

The following traits have been repeatedly observed and are determined to be basic characteristics of Praeludium which in combination distinguish this geranium as a new and distinct cultivar:

1. Intensive-red colored flower;
2. Semi-double flower form;
3. Dark green foliage with a slight zonation;
4. Robust foliage;
5. Large umbel;

6. Good rooting pattern.

Of the many commercial cultivars known to the present inventors, the most similar in comparison to Praeludium is Alex. In comparison to Alex, Praeludium has a larger umbel, a higher peduncle, slight zonation of the foliage.

The accompanying photographic drawing shows typical flower and foliage characteristics of Praeludium, with colors being as true as possible with illustrations of this type.

In the following description color references are made to The Royal Horticultural Society Colour Chart. The color values were determined between 10:00–11:30 a.m. on Sept. 3, 1986 under natural light at Rheinberg in a room with orientation to the north.

Classification:

*Botanical.*—*Pelargonium zonale* cv Praeludium.

*Commercial.*—Geranium.

Inflorescence

A. Umbel:
- *Average diameter.*—10 to 12 cm.
- *Average depth.*—6 to 7 cm.
- *Peduncle length.*—8 to 10 cm.
- *Pedicel length.*—2.5 to 3 cm.

B. Corolla:
- *Average diameter.*—5 to 6 cm.
- *Form.*—Semi-double.
- *Color (general tonality from a distance of three meters).*—ca. RHS 40 A to 44 B.
- *Color (abaxial).*—ca. RHS 40 A to 44 B.
- *Color (adaxial).*—ca. RHS 41 A to 43 B.

C. Bud:
- *Shape.*—Elliptic.
- *Color (abaxial).*—ca. RHS 40 A.
- *Color (adaxial).*—ca. RHS 40 A.

D. Reproductive organs:
- *Androecium.*—Obdiplostemon, centrifugal dedouplement, fertil.
- *Gynoecium.*—5-lobed stigma, pubescent, 5 carpels, coenocarp hypogyn.

E. Spring flowering response period:
- *FRG.*—50% of plants with at least one flower open 16 weeks after stick of unrooted cuttings.

F. Outdoor flower production: Good.

G. Durability: Good.

Plant

A. Foliage:
*Form.*—Kidney shaped.
*Margin.*—Undulate, bicrenate.
*Color (abaxial).*—ca. RHS 136 B.
*Color (adaxial).*—ca. RHS 138 B to 136 C.
*Color (zonation).*—ca. RHS 136 A.
*Tolerance of botrytis.*—*Good.*

B. General appearance and form:
*Internode length.*—Normal.
*Branching pattern.*—Good.

*Height.*—Relatively tall.

I claim:

1. A new and distinct cultivar of geranium known as *Pelagonium zonale,* to be known by the cultivar name Praeludium, as described and illustrated, and particularly characterized by the combination of characteristics of: an intensive-red colored flower; a semi-double flower form; a dark green foliage with a slight zonation; robust foliage; a large umbel; and a good rooting pattern.

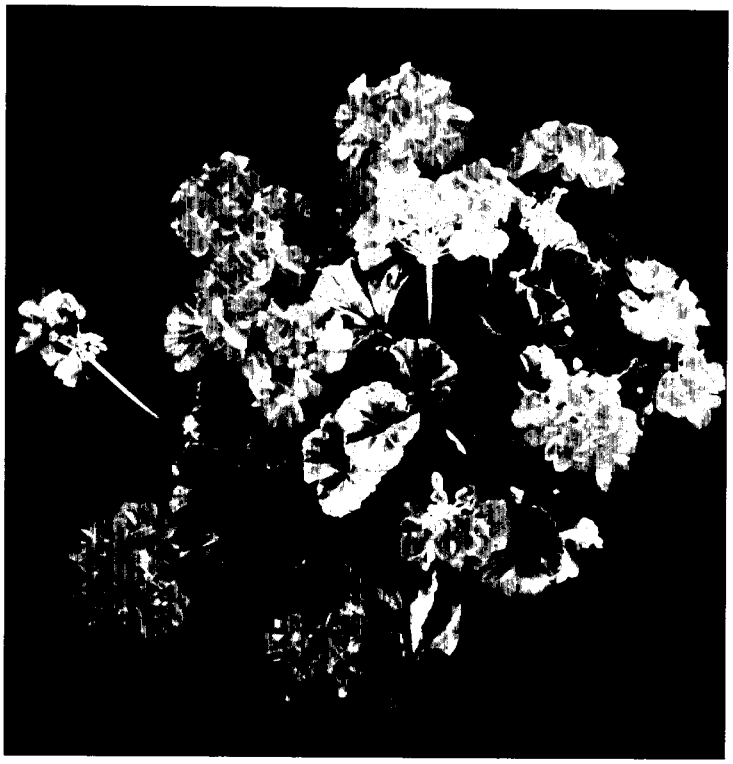

* * * * *